United States Patent [19]

Bahar

[11] Patent Number: 4,952,517

[45] Date of Patent: Aug. 28, 1990

[54] POSITIVE STEP IMMUNOASSAY

[75] Inventor: Izak Bahar, Chestnut Hill, Mass.

[73] Assignee: Hygeia Sciences, Inc., Newton, Mass.

[21] Appl. No.: 153,081

[22] Filed: Feb. 8, 1988

[51] Int. Cl.$^5$ .................... G01N 33/53; G01N 33/543
[52] U.S. Cl. ..................................... 436/518; 436/501;
    436/523; 436/528; 436/533; 436/535; 436/536;
    435/7; 422/61
[58] Field of Search ............... 436/501, 909, 533, 518,
    436/523, 528, 535, 536; 435/7

[56] References Cited

U.S. PATENT DOCUMENTS

| 4,283,383 | 8/1981 | Masson et al. | 424/12 |
| 4,313,734 | 2/1982 | Leuvering | 23/230 |

FOREIGN PATENT DOCUMENTS

| 1183080 | 2/1985 | Canada . |
| 0086095 | 8/1983 | European Pat. Off. . |
| 0114614 | 8/1984 | European Pat. Off. . |
| 0158746 | 10/1985 | European Pat. Off. . |
| 2029011 | 3/1980 | United Kingdom . |

OTHER PUBLICATIONS

Ruddy in "Manual of Clinical Laboratory Immunology", 3rd Ed., Editors, Rose, Friedman and Fahey, ASM, Wash., D.C., 1986, pp. 175–184.
Toth et al. in "Manual of Clinical Laboratory Immunology", 3rd Edition, Editors: Rose, Friedman and Fahey, ASM, Wash., D.C., pp. 204–210.

Primary Examiner—Christine M. Nucker
Assistant Examiner—Karen I. Krupen
Attorney, Agent, or Firm—Staas & Halsey

[57] ABSTRACT

An assay procedure that is particularly valuable for detecting and/or determining the presence of threshold levels of analyte ligands in biological fluids. In one particularized and specialized aspect the disclosure is directed to procedures for detecting and/or determining threshold levels of hormone metabolites such as pregnanediol-3-glucuronide ($P_3G$) and estrone-3-glucuronide ($E_1 3G$) in human urine. The assay consists of contacting a sample containing the analyte with a known amount of an antibody thereto and with a calibrated amount of the analyte itself that is conjugated to said solid support. When the level of the analyte in the sample exceeds a threshold level, such as 5 ug/ml for $P_3G$, the antibody will be insufficient to block all of the corresponding analyte on the solid support. Thus, upon addition of labelled antibody to the assay system, a detectable immunoreaction product becomes attached to the support to indicate that the amount of analyte in the sample exceeds the threshold level. On the other hand, if the level of the analyte in the sample is below the threshold amount, the free antibody will be sufficient to block all of the corresponding analyte on the solid support preventing labelled antibody from forming a detectable immunoreaction product on the support and thus no signal will appear.

42 Claims, No Drawings

POSITIVE STEP IMMUNOASSAY

BACKGROUND OF THE INVENTION

1. Field of the Invention

The present invention relates to procedures for the determination and/or detection of immunologically reactive analytes such as ligands and ligand receptors. More particularly, the invention relates to methodology that is valuable for determining and/or detecting the presence of threshold levels of analytes such as therapeutic drugs, toxic materials, drugs of abuse and hormones and the like that are indicative of a physiological condition. In this latter regard, in one particularized aspect, the invention relates to procedures for detecting the presence of threshold levels of hormones such as progestin and estrogen derivatives and luteinizing hormone (LH) in human urine samples. The invention also relates to kits of materials for use in conducting such assay procedures.

2. Description of the Prior State of the Art

There has long been a need for measuring substances with a high degree of sensitivity and specificity. In particular, in fields such a clinical medicine, forensic science, environmental quality testing, food quality assurance, drug testing and other related areas, the presence and/or amount of trace substances in test samples is often of great significance. In such areas, the measurement of very low concentrations in the order of parts per million or less is often necessary. Moreover, such testing or measurement generally requires the identification of particular molecules while not sensing other molecules with similar yet different structures.

The need for sensitive and specific tests has been addressed in the past by the development of a number of immunoassay procedures based on the highly specific and sensitive interaction between an antigen and an antibody directed against such antigen. Antigens and antibodies are initially recognized as being the participants in the immune process of an animal, that is, when an animal is injected with a foreign substance that is an antigen, the animal in time responds by producing antibodies which are protein molecules that recognize and tightly bind the invading antigen thereby facilitating removal or destruction of the latter. The immune process is highly specific and the use of immunoassay procedures for identification of specific substances has been exploited with great success. Such procedures have been further facilitated by the important discovery of Milstein and Kohler reported in Nature 256: 495–497, 1975 which concerns the preparation of so-called monoclonal antibodies. The details of this work are well known and there is no need to repeat the same here; however, as a result of the Milstein and Kohler work, the development of highly sensitive and specific reagents has been particularly facilitated.

Known assay procedures include radioimmunoassay (RIA) procedures, enzyme immunoassays (EIA), enzyme linked immunosorbant assays (ELISA), fluorescent assays, chemiluminescence assays and assays wherein metal particles such as gold sol particles are used as tags or labels. These prior procedures are referred to and described in a commonly assigned, copending application Ser. No. 105,285, filed Oct. 7, 1987, the entirety of which is hereby specifically incorporated by reference.

Some of the known assays operate on the basis of a competitive immunoreaction. In performing competitive immunoassays, one generally mixes (1) a first immunoreactive substance (contained in an unknown sample), (2) a second immunoreactive substance that is specifically reactive with the first substance, and (3) a quantity of a third immunoreactive substance that has immunological reaction characteristics that are immunospecifically the same as the immunological reaction characteristics of the first immunoreactive substance. The third substance carries a detectable tag. During the course of the immunoreaction, the first and third substances compete with one another for binding sites on the second substance. After a predetermined time of immunoreaction, the second substance is separated and the amount of third substance bound thereto is determined. If the first substance is initially present at low levels, then the amount of third substance and therefore the amount of detectable tag bound to the second substance will be elevated. On the other hand, if the amount of first substance is elevated, then the amount of detectable tag bound to the second substance via the third substance will be low. Thus, at all levels, the amount of detectable tag which becomes bound to the second substance will be inversely proportional to the amount of first immunoreactive substance in the sample. At intermediate levels, the amount of detectable tag bound to the second substance is monotonically and inversely proportional to the level of the first immunoreactive substance in the sample.

Competitive immunoassays have found widespread use in clinical laboratories yielding accurate measurements of a great number of clinically relevant analytes. However, there are two features of the competitive assay format that are less than highly desirable outside of a sophisticated clinical laboratory setting. First, as discussed above, the resulting signal is inversely proportional to the amount of substance to be detected. In the ideal case, however, one would prefer that elevated levels of analyte should produce elevated levels of signal. Thus, in a non-instrumental, e.g. visual, examination, the amount of signal produced would be directly proportional to the amount of analyte detected. Secondly, in the competitive immunoassay format described above, the amount of detectable signal changes as a monotonically decreasing function of the amount of analyte in the sample. Thus, for analyte levels that are very close to one another, only modest shifts in signal intensity are produced. Such modest shift, although readily detectable with modern instrumentation, may often be too subtle for reliable detection by the human eye for direct visual examination purposes.

Where toxic and/or environmentally undesirable substances are concerned, once a non-hazardous threshold level has been selected as a criteria, it is advantageous to use tests which provide a completely negative result at levels even minutely below the threshold level and yet provide a clear positive indication when the level exceeds the selected threshold level.

In a more specific sense, there has long been a need for simple yet reliable methodology for determining the human fertile period during the menstrual cycle, that is, the period in which viable sperm and a viable ovum may both be present in the reproductive tract of the female. For a variety of reasons, contraceptive devices and materials may not be available for use, and accordingly, techniques for ascertaining the fertile period of the menstrual cycle have become desirable. Manifestly, techniques for ascertaining the fertile period of the menstrual cycle are valuable both for intentionally avoiding pregnancy and for facilitating conception when pregnancy is desired.

The menstrual cycle is governed by the release of hormones from the female glands and organs. Such release is predictable and specifically related to ovulation by which ova are released from the ovaries and the lining of the uterus is made ready for pregnancy and the hormones and/or metabolites thereof find their way into the urine. The specific biological phenomena are described in detail and with clarity in European Patent Publication No. 0086095, which was published on August 17, 1983 in European Patent Office Bulletin 83/33. And suffice it to say that during a normal menstrual cycle, the level of estrone-3-glucuronide ($E_1 3G$) in female urine begins to rise about 6 days prior to ovulation and reaches its peak about 1 day before ovulation and falls rapidly during and after ovulation. The level of pregnanediol-3-glucuronide ($P_3 G$) in female urine begins to rise on the day of ovulation, and reaches a peak 2 to 3 days after ovulation and remains elevated for the duration of the luteal phase. Likewise, the relationship between $P_3 G$ and $E_1 3G$ levels is well known, and from the '095 European patent publication identified above, the ratio of estrogen to progestin metabolites in the urine has been found to be useful in monitoring the progress of the menstrual cycle.

Of particular importance in following the menstrual cycle by determining hormonal activity is the fact that approximately during ovulation, the level of $P_3 G$ in the urine surges to levels above 4 ug/ml. Thus, a simple and reliable assay capable of determining and/or detecting the presence of at least such threshold amount of $P_3 G$ in urine would be extremely valuable in determining whether ovulation has occurred.

SUMMARY OF THE INVENTION

The positive step immunoassay procedure of the present invention addresses each of the drawbacks inherent in prior art competitive immunoassays. Firstly, inasmuch as the reaction is positive, elevated signals appear in the presence of elevated analyte levels. Moreover, in accordance with the positive step function of the immunoassays of the present invention, one does not observe monotonic decrease (or increase) in signal as a function of analyte concentration, but rather, the level of signal unexpectedly rises quite sharply at a preselected threshold. That is to say, analyte levels just slightly below the selected threshold result in low or barely detectable signal levels, while analyte levels just above the threshold produce the full level of signal attainable with the articular label that is utilized.

The present invention provides methodology and kits of materials useful in connection with immunoassays generally. In particular, the invention provides a positive step assay which produces a signal in the presence of threshold levels of an immunoreactive substance. Conventional assays may rely upon competition between labelled and unlabelled immunoreactive substances, depending on the format, and the positive step assay of the present invention reverses the signal so that the user is able to easily ascertain the presence of the immunoreactive substance in the sample. Thus, through the use of the present invention, the detection of surges in the levels of hormones such as $P_3 G$, $E_1 3G$ and LH in urine is facilitated.

The positive step immunoassay format of the present invention has important application in areas other than fertility testing. In this regard, there are a variety of situations in which the determination of the actual amount of a substance present in a sample may be less significant than whether the substance is present in an amount that is above or below a certain threshold level. One example that immediately presents itself is in the area of forensic testing for controlled or abused drugs. For example, a threshold value of 0.1% is important in testing for alcohol levels in blood since values greater than 0.1% are considered to be evidence of intoxication. Similarly, for marijuana or THC, urine levels of 10, or in other cases 100 ng/ml, are considered to be proof of substance abuse. Obviously, the positive step immunoassay formats of the present invention, which produce no color at analyte levels below a threshold amount and wherein coloration is achieved at analyte levels above the threshold amount, are applicable in such context.

The positive step immunoassay of the present invention is also applicable in the field of therapeutic drug monitoring. There are a number of highly useful therapeutic drugs such as theophylline (an antiasthmatic), digoxin (a cardiac regulator) and aminoglycoside antibiotics, to name a few, which are characterized by a therapeutic window. The therapeutic window is the range of concentrations of the particular drug from the minimum level for therapeutic effectiveness up to the level wherein unwanted or toxic reactions may occur. Clearly, a dual positive step immunoassay with one assay calibrated to detect the minimum therapeutic threshold and the other calibrated to detect the toxic threshold would be extremely valuable.

In accordance with the invention, an immunoassay procedure is provided to determine the initial presence of at least a prespecified (threshold) amount of a first immunoreactive substance in a liquid sample. The procedure comprises the steps of first establishing an immunochemical reaction phase by admixing a liquid sample containing an initially unknown amount of the first immunoreactive substance with (1) a known amount of a second immunoreactive substance that is specifically immunoreactive with said first substance and (2) a quantity of a third immunoreactive substance that has immunological reaction characteristics which are immunospecifically the same as the immunological reaction characteristics of the first immunoreactive substance. In accordance with the invention, the known amount of the second substance should be immunochemically equivalent (just sufficient to immunospecifically bind) to the total of the prespecified threshold amount of first substance and said quantity of third immunoreactive substance. Thus, when the amount of the first immunoreactive substance in the liquid sample solution exceeds the prespecified threshold amount thereof, unreacted third substance will be available for further immunospecific reaction in the reaction phase. The reaction phase thus established is then contacted with a quantity of a fourth immunoreactive substance that has immunological reaction characteristics which are immunospecifically the same as the immunological reaction characteristics of the second substance. And the fourth substance carries a detectable tag. Thus, the initial presence of more than the prespecified threshold amount of first substance in the sample may be determined by detecting the existence of a specific immunoreaction product which contains the detectable tag.

Preferably, the third immunoreactive substance will be bound to a solid support whereby the third immunoreactive substance is immobilized (such as where the solid support comprises a permeable membrane), or is rendered collectible (such as where the solid support comprises a dispersible, particulate, collectible solid material).

In a preferred form of the invention, the liquid sample containing the first immunoreactive substance is premixed with a known amount of a second immunoreactive substance that is immunospecifically reactive with said first immunoreactive substance, to thereby produce a first reaction phase. The first reaction phase is then contacted with a quantity of the third immunoreactive substance to produce a second reaction phase. In this form the invention is particularly useful in performing an assay for small molecules including drugs and haptens such as $P_3G$ and $E_13G$.

In a preferred practical form of the invention for determining the amount of a first immunoreaction substance in a liquid sample, the immunoassay procedure of the invention comprises the steps of furnishing a liquid sample containing an initially unknown amount of the first immunoreactive substance and dividing the sample into a plurality of aliquot portions. Respective different amounts of a second immunoreactive substance that is specifically immunoreactive with said first immunoreactive substance are introduced into the aliquot portions to produce a plurality of first reaction phases, each of which contains a respective different known amount of the second substance. The first reaction phases are then contacted with a quantity of a third immunoreactive substance that has immunological reaction characteristics which are immunospecifically the same as the immunoreaction characteristic of the first immunoreactive substance. Thus, a plurality of second reaction phases are produced, each containing the same amount of the third substance and respective different amounts of the second substance. In accordance with the invention, the respective known amounts of the second substance in the second reaction phases are predetermined so as to be immunospecifically equivalent to (just enough to immunospecifically react with and block) the total of said quantity of third substance plus a corresponding respective preselected amount of the first substance, whereby, when the unknown amount of the first substance in the sample is less than or equal to the corresponding respective preselected amount thereof, no unreacted third substance will be available for further immunospecific reaction in the second reaction phase. And when the unknown amount of the first substance in the sample is greater than the corresponding respective preselected amount thereof, unreacted third substance will be available for further immunospecific reaction in the corresponding second reaction phase. The second reaction phases are then brought into contact with a quantity of a labelled fourth immunoreactive substance having immunological reaction characteristics that are immunospecifically the same as the immunological reaction characteristics of the second substance. Thus is produced a plurality of respective detection phases corresponding respectively to the second reaction phases, whereby a labelled immunoreaction product will be formed by specific immunoreaction between unreacted third substance and labelled fourth substance in each reaction phase which corresponds to a second phase where the amount of first substance in the sample exceeds the said corresponding respective preselected (threshold) amount thereof. The presence or absence of labelled immunoreaction product may then be detected in each detection phase as an indication of the initial presence of at least the corresponding respective preselected amount of first substance in the sample.

Through the use of the procedure just described, the amount of the first immunoreactive substance in the liquid sample may be determined to be within a specific narrow range depending on the respective calibrated amount of the second immunoreactive substance that is introduced into the various reaction phases. That is to say, a first reaction system may be calibrated so that the corresponding reaction phase will contain labelled immunoreaction product when the amount of first immunoreactive substance in the sample is greater than 1 ug/ml, a second reaction system may be calibrated so that the corresponding reaction phase will contain labelled immunoreaction product when the level of first immunoreactive substance in the sample is greater than 2 ug/ml, a third reaction system may be calibrated so that the corresponding reaction phase will contain labelled immunoreaction product when the amount of first immunoreactive substance in the liquid sample exceeds 3 ug/ml, and so on. Thus, and if the procedure is designed so that the presence of labelled immunoreaction product in the detection phase produces coloration, the detection phases of systems precalibrated to detect levels less than the determined amount of first immunoreactive substance will be colored, while the detection phases of the systems precalibrated to detect levels greater than the determined amount of first immunoreactive substance will be free of color.

In another important aspect of the invention, a kit of materials is provided for conducting an immunoassay procedure to detect the presence of at least a predetermined amount of a first immunoreactive substance in a liquid sample. The kit comprises a known amount of second immunoreactive substance that is specifically immunoreactive with the first substance, a known amount of a third immunoreactive substance that has immunological reaction characteristics which are immunospecifically the same as the immunological reaction characteristics of the first immunoreactive substance, and an amount of a labelled fourth immunoreactive substance having immunological reaction characteristics which are immunospecifically the same as the immunological reaction characteristics of the second substance. The third immunoreactive substance may preferably be bound to a solid support, and in a particularly preferred aspect of the invention, the solid support may comprise a dispersible, particulate, collectible solid material. In an even more preferred aspect of the invention, the fourth immunoreactive substance may be labelled using a gold sol particle tag capable of producing a red coloration on a filter element when materials containing the tag are collected thereon.

While the present invention is useful in connection with all immunoreactive substances, that is specific binding proteins and corresponding bindable substances, the invention has particular utility in connection with small monoepitopic molecules such as drugs and haptens that are hormones and hormonal metabolites including $P_3G$ and $E_13G$ and related materials generated by human females during the menstrual cycle.

DESCRIPTION OF THE SPECIFIC ASPECTS OF THE INVENTION

In all of the aspects of the invention set forth above, the third immunoreactive substance that has immunological reaction characteristics which are immunospecifically the same as the immunological reaction characteristics of the first immunoreactive substance will generally be of basically the same substance as the first immunoreactive substance. That is to say, if the procedure and/or kit is for the purpose of determining the initial presence of $P_3G$ in a liquid sample, the third immunoreactive substance will most generally also comprise $P_3G$. Similarly, the fourth immunoreactive substance most generally will be the same as the second immunoreactive substance, each being the same antibody to the hormone. In this regard, if the first immunoreactive substance is such that it has multiple immunoreactive sites available for immunoreaction, the second and fourth immunoreactive substances should be specifically immunoreactive relative to the same site or sites.

In accordance with the present invention, the positive step assay format changes an inverse competitive signal to a positive step in the presence of increasing levels of hapten or other immunoreactive substance in the liquid sample. Additionally, the assay format may be designed to provide a positive signal at a predetermined level of immunoreactive substance in the liquid sample (for example, the threshold level of $P_3G$ indicating that ovulation has occurred) and no signal at a lower level. Since the physiological detection of $P_3G$ is important between 2.5 and 5 ug/ml in urine samples, the assay may be constructed, for example, to give no signal at 2.5 ug/ml, but maximal signal at 5 ug/ml of $P_3G$.

The present invention provides an assay procedure and a kit of materials for determining and/or detecting a variety of immunological reactive analytes such as ligands and ligand receptors in aqueous samples. The analytes are immunoreactive substances such as mono or polyepitopic ligands, including both antigens and haptens; however, the invention is particularly useful in connection with monoepitopic haptens such as hormones and especially the metabolites of estrogen and progestin compounds such as $E_1 3G$ and $P_3G$. A characteristic of the immunoreactive substances with which the present invention is involved is that the same are capable of immunospecifically binding another immunoreactive substance. When one immunoreactive substance is specifically immunoreactive with another immunoreactive substance, one of the substances, or molecules, is referred to as the ligand, and the other as the receptor o anti-ligand. The molecules are different and one has an area on the surface or in a cavity which specifically binds to a particular spatial and/or polar organization of the other.

When an immunoreactive substance is admixed with an immunoreactive substance that is specifically immunoreactive therewith, the two present an immunochemical reaction phase which, if sufficient time for incubation is available, will result in the occurrence of a specific immunoreaction between the two substances so as to generate an immunoreaction product.

Antigenic immunoreactive substances may have one or more epitopes which are capable of entering into immunospecific reaction. These epitopes may be the same or different. however, only those epitopes that are the same are capable of entering into a specific immunoreaction with a given binding partner. If an immunochemical reaction phase is allowed to incubate for a sufficient amount of time, the reaction will go to equilibrium such that when the amounts of immunospecifically reactive substances are immunochemically equivalent, no further sites are available for immunospecific reaction. When this state is achieved, it can be said that no unreacted immunoreactive substance is available for immunospecific reaction in the reaction phase. And if one or the other of the specifically immunoreactive materials is present in an amount which is greater than the immunochemical equivalent amount, none of the other immunoreactive substance will be available in the reaction phase for further immunospecific reaction. Thus, such other immunoreactive substance is said to be blocked.

Manifestly, the specific immunochemical equivalency of any given immunoreactive substance is not a precise, mathematically calculatable number. Rather, the specific immunochemical equivalency of any given immunoreactive substance relative to another immunoreactive substance that is specifically immunoreactive therewith is generally determined empirically. This may be done, in the present case, simply by setting up a number of standards containing different amounts of the unknown material and determining, by experimentation, the amount of the other substance it takes to block the first substance. For example, such determination may be accomplished by titration in accordance with well-known procedures.

In accordance with the present invention, an immunoreactive substance is said to have immunological reaction characteristics which are immunospecifically the same as the immunological reaction characteristics of another substance when those two substances are capable of entering into the identical specific immunochemical reaction. That is to say, the substances are capable of immunospecific reaction in an analogous manner. This phenomena may occur, for example, when one of the substances is a portion of the other substance and carries the same specific epitope. The phenomena may also occur when the substances are basically the same but one is freely mobile in the reaction phase and the other is immobilized and/or conjugated to a solid phase which facilitates collection. The phenomena may also be present when one of the substances is present in its basic and unreacted form and the other is labelled or tagged with a detectable tag which facilitates identification and/or quantification as a part of the assay procedure. Generally speaking, in the case of the present invention, a hapten which is free in the reaction phase, and the same hapten which is conjugated to a solid support, have immunological reaction characteristics which are immunospecifically the same. Also, an anti-hapten antibody which is labelled with a detectable tag has immunological reaction characteristics which are immunospecifically the same as the immunological reaction characteristics of the same anti-hapten antibody that is not labelled. Such substances may be said to have analogous immunological reaction characteristics.

In connection with the present invention, when the unknown amount of immunoreactive substance in the liquid sample exceeds the prespecified or threshold amount, the result is the production of a labelled immunoreaction product. The labelled immunoreaction product may be in the form of an immunoreaction product (or composite) which is either immobilized by being bound to a solid support such as a membrane, or is bound to an initially dispersed dispersible, particulate, collectible solid material that has been collected, for example on a filter element. In either case, the immunoreaction product carries a tag which is colored in its own right, such as a gold sol particle, or which facilitates a color forming reaction, such as in the case of enzymatic color formation. In enzymatic color forming systems, the color forming materials are brought together into a color forming condition by formation of the immunoreaction product. Such procedures and materials are well known and need not be discussed in further detail here. The formation of a detectable color as a result of a gold sol particle tag is part of the invention disclosed and claimed in said co-pending application Ser. No. 105,285, referred to above. Suffice it to say that the gold sol particles are collected and concentrated by the formation of the immunoreaction product and collection of the same such that a visually observable coloration is formed.

The invention is more fully described with reference to the following specific examples.

EXAMPLE 1

Plate ELISA Assay Using Positive Step Procedure
Preparation of Gelatin - $P_3G$

Pregnanediol-3-glucuronide ($P_3G$) (Sigma) in the free acid form was covalently coupled to gelatin (Sigma) by the mixed acid anhydride method, exactly as described by Erlanger et al., *J. Biol. Chem.* 228, 713–727 (1957). By this procedure, the steroid is joined as a peptide bond via the glucuronide carboxylic acid to E-amino groups of lysine residues in the polypeptide chain of the protein.

Attachment of Gelatin - $P_3G$ to Solid Support

Gelatin-$P_3G$ prepared as set forth above was passively adsorbed to the plates of a PVC 96 well microtiter plate. 50 ul of a gelatin-$P_3G$ solution containing 0.250 ug/ml of the steroid in a solution containing 10 mM $KPO_4$ and 0.145 M NaCl (pH 7.4) (PBS) was added to each of the wells and the solution was allowed to stand on the plates in the wells for one hour at room temperature (22° C.). The solution was then decanted from the wells and the plates were blocked to avoid non-specific binding by contacting the same with a PBS/0.02% NaAzide solution (pH 7.2) containing 1% gelatin for a period of one hour at room temperature. The treated wells were again decanted and washed two times with a PBS solution containing 0.1% Tween 20 (v/v) (pH 7.4).

Plate ELISA Assay

Standard solutions containing anti-$P_3G$ antibody in PBS were provided in eight different concentrations, i.e., 1.0, 2.0, 4.0, 8.0, 16.0, 32.0, 64.0 and 128.0 ug/ml, and sample solutions containing $P_3G$ in PBS were provided in six different concentrations, i.e., 2.5, 1.25, 0.625, 0.3125, 0.156, and 0 ug/ml. 150 ul of each anti-$P_3G$ antibody standard solution was admixed with 30 ul of each $P_3G$ sample solution to provide 48 separate reaction phases. Two separate 60 ul portions of each reaction phase was placed in the wells.

The solutions were allowed to incubate in the wells for 15 minutes at room temperature. The solutions were then decanted from the wells and the plates were washed two times with a wash solution comprising 0.1% Tween 20 in PBS. 50 ul of a solution containing 62.5 ng/ml of an anti-$P_3G$ antibody/horseradish peroxidase (HRP) conjugate (prepared by the well known method of Nakane et al.) in 0.1 M Tris-acetate (pH 7.0) was added to each plate and allowed to incubate for 15 minutes at room temperature. The wells were then washed five times with the PBS/Tween wash solution to make sure that all non-specifically bound HRP is removed. 50 ul of a color developing substrate solution comprising a fresh mixture of 3 ml. of 0.125% tetramethylbenzidine in methanol and 7 ml. of 0.03% hydrogen peroxide in a 0.1 M phosphate and 50 mM citric acid aqueous solution (pH 5.0) was added to each plate and allowed to react for 5 minutes at room temperature. The intensity of the color formation was read on a Dynatech plate reader (Dynatech, Virginia) at 630 nm with a reference wave length of 490 nm. The results are set forth in Table I below:

TABLE I

| Concentration of Anti-$P_3G$ Antibody, ug/ml | Concentration of $P_3G$, ug/ml | | | | | |
|---|---|---|---|---|---|---|
| | 2.5 | 1.25 | 0.625 | 0.3125 | 0.156 | 0 |
| 1 | 0.451 | 0.572 | 0.604 | 0.649 | 0.688 | 0.026 |
| 1 | 0.440 | 0.487 | 0.587 | 0.589 | 0.598 | 0.028 |
| 2 | 0.714 | 0.757 | 0.751 | 0.744 | 0.481 | 0.016 |
| 2 | 0.684 | 0.703 | 0.725 | 0.708 | 0.514 | 0.018 |
| 4 | 0.468 | 0.503 | 0.554 | 0.576 | 0.030 | 0.013 |
| 4 | 0.505 | 0.503 | 0.564 | 0.549 | 0.022 | 0.010 |
| 8 | 0.678 | 0.695 | 0.743 | 0.659 | 0.016 | 0.011 |
| 8 | 0.641 | 0.712 | 0.750 | 0.654 | 0.016 | 0.010 |
| 16 | 0.478 | 0.537 | 0.480 | 0.011 | 0.000 | 0.000 |
| 16 | 0.469 | 0.537 | 0.521 | 0.008 | 0.002 | 0.002 |
| 32 | 0.613 | 0.619 | 0.019 | 0.010 | 0.004 | 0.006 |
| 32 | 0.633 | 0.547 | 0.021 | 0.011 | 0.006 | 0.010 |
| 64 | 0.477 | 0.004 | 0.004 | 0.002 | 0.002 | 0.000 |
| 64 | 0.511 | 0.007 | 0.004 | 0.003 | 0.000 | 0.000 |
| 128 | 0.009 | 0.007 | 0.007 | 0.007 | 0.006 | 0.011 |
| 128 | 0.009 | 0.008 | 0.009 | 0.010 | 0.012 | 0.013 |

This test of Example 1 was arranged to illustrate the detection and determination of $P_3G$ in the sample solutions, and the detection and determination of whether the amount of $P_3G$ in a given sample solution exceeds a particular known preselected amount. The $P_3G$ in the sample solution may be referred to as a first immunoreactive substance, the anti-$P_3G$ antibody in the standard solutions may be referred to as a second immunoreactive substance. The first and second immunoreactive substances are specifically immunoreactive with one another. The $P_3G$ bound to the plate (a solid support) by gelatin linkage is a third immunoreactive substance which is analogous to the first immunoreactive substance and thus has immunological reaction characteristics which are immunospecifically the same as the immunological reaction characteristics of $P_3G$, the first immunoreactive substance. The anti-$P_3G$ antibody which is conjugated to HRP is a fourth immunoreactive substance that is analogous to the second immunoreactive substance and thus has immunological reaction characteristics which are immunospecifically the same as the immunological reaction characteristics of the second substance. The HRP that is conjugated to the anti-$P_3G$ antibody is an enzymatic tag or label that is capable of being detected by known means and procedures. Thus, the anti-$P_3G$ antibody/HRP conjugate is a labelled fourth immunoreactive substance.

In the Example 1 illustration, a known amount of anti-$P_3G$ antibody (second immunoreactive substance) is contacted with preselected amounts of $P_3G$ (first immunoreactive substance). $P_3G$ ordinarily will be an analyte to be detected or determined, but for purposes of the present illustrative example, the $P_3G$ is present in known amounts. Thus is provided a series of first reaction phases, each containing respective different known amounts of anti-$P_3G$ antibody. The first reaction phases are then each brought into contact with the $P_3G$ (third immunoreactive substance) that is bound to the respective plates of the microtiter plate to produce a second reaction phase in each well of the microtiter plate. The plates of the wells were all contacted by the same $P_3G$-gelatin solution under identical conditions, and thus the second reaction phases contain the same amount of $P_3G$ bound to the plate and respective different known amounts of anti-$P_3G$ antibody.

In each second reaction phase, if the total known amount of anti-$P_3G$ antibody is sufficient to immunospecifically react with all of the $P_3G$ in the sample and all of the bound $P_3G$, the bound $P_3G$ is said to be blocked by the antibody and further immunoreaction is prevented. However, if the total amount of anti-$P_3G$ antibody is not sufficient to react with all of the $P_3G$ in the second reaction phase, bound $P_3G$ will remain unblocked and available for further immunospecific reaction. Thus, when the second reaction phases are washed and contacted with the anti-$P_3G$ antibody/HRP conjugate solution, immunospecific reaction will occur in those cells where unblocked bound $P_3G$ was present (where the $P_3G$ in the sample exceeded the calibrated amount) and the HRP enzymatic color former will be bound to the plate via the immunoreaction between the unblocked $P_3G$ and the antibody/HRP conjugate. Manifestly, as the amount of $P_3G$ in the sample increases, the ability of a given quantity of antibody to block the bound $P_3G$ decreases. At an empirically determinable point, further increase in $P_3G$ in the sample results in the presence of unblocked $P_3G$ on the plate and subsequent binding of HRP to the plate upon introduction of the labelled antibody. When HRP is thus bound to the plate, color is formed by addition of the TMB solution.

In Table I it can be seen (right hand column) that no color was produced in the cells where there was no $P_3G$ in the sample. (The numerical values in Table I increase directly with increased color, and the very small numbers indicate very little color while the relatively much larger numbers indicate a distinct coloration.) Also, in the bottom row of Table I, where the known concentration of anti-$P_3G$ antibody was 128 ug/ml, no color was produced in any of the cells since this amount of antibody was sufficient to block all of the $P_3G$, even when the concentration of $P_3G$ in the sample was 2.5 ug/ml. However, in the case where the antibody concentration was 64 ug/ml, full coloration of the plate occurred when the concentration of $P_3G$ in the sample reached 2.5 ug/ml; where the antibody concentration was 32 ug/ml, full coloration occurred at a $P_3G$ concentration of 1.25 ug/ml; where the antibody concentration was 16 ug/ml, full coloration occurred at a $P_3G$ concentration of 0.625 ug/ml; at an antibody concentration of 8 ug/ml, the jump occurred at 0.3125 ug/ml of $P_3G$; and where the antibody concentration was 1 or 2 ug/ml, the jump occurred at 0.156 ug/ml of $P_3G$. Manifestly, it can be seen that the jump point from no color to full color is extremely sensitive and may be adjusted and calibrated empirically simply by modifying the amount of anti-$P_3G$ antibody in the standard solution and/or the amount of $P_3G$ bound to the support.

EXAMPLE 2

Flow Through ELISA Assay Using Positive Step Procedure

Preparation of Membrane

A microporous flow through membrane was used to support a solid phase immobilized reactant in this example. The membrane used was a Pall immunoaffinity membrane of the sort described in U.S. letters Pat. No. 4,066,512. The membrane was prepared by spotting the same with 3 ul of a solution containing gelatin-$P_3G$ prepared as described above in Example 1 and 100 ug/ml of glucose oxidase in PBS. In all, five sets of spotted membranes were prepared using different concentrations of gelatin-$P_3G$, i.e., 10, 1, 0.1, 0.01 and 0.001 ug/ml. The spotted membranes were blocked to avoid nonspecific binding using 2 ml of a solution containing 0.5% Carnation milk and 0.02% Tween 20 in PBS (pH 7.4). The membranes were then installed in flow through devices of the type described in commonly assigned, co-pending application Ser. No. 107,240, filed Oct. 13, 1987.

Flow Through Assay

An anti-$P_3G$ antibody standard solution containing 32 ug/ml of the antibody in PBS, and sample solutions containing respectively 2.5, 1.25 and 0 ug/ml of $P_3G$ in PBS were provided. 40 ul of each sample solution was premixed with 400 ul of the antibody standard solution and the mixtures were poured separately onto and through the membrane of a respective flow through device prepared as described above. 400 ul an anti$P_3G$ antibody/HRP conjugate solution prepared as described in Example 1 was then poured through each membrane and the membranes were washed with 1 ml of a wash solution containing 3% Igepal and 1% sodium dodecyl sulphate in PBS. The membranes were then contacted with 0.4 ml of a substrate solution consisting of an admixture of 7 parts of a solution containing 7.0% dextrose and 0.01% TMB in 0.034 M citrate 0.071 M sodium phosphate and 3 parts methanol. The results, evaluated visually after 3 to 5 minutes, did not vary with the concentration of the spotting solution, and were as follows:

| $P_3G$ (ug/ml) | Reading |
|---|---|
| 2.5 | + (blue color) |
| 1.25 | — |
| 0 | — |

EXAMPLE 3

Sol Capture Assay Using Positive Step Procedure

Preparation of Solid Phase Particles

A latex-gel-$P_3G$ dispersion was prepared by covalently coupling $P_3G$ to gelatin as set forth above (Example 1) and coupling the gelatin-$P_3G$ component to Polybead carboxylate monodisperse microspheres using exactly the same procedure as is described in Example II(g) of said application serial no. 105,285 cited above. A series of sample solutions, respectively containing 0.625, 1.25, 2.5, 5.0, 10 and 20 ug/ml of $P_3G$ in PBS, were provided. 20 ul of each sample solution was premixed with 300 ul of the antibody standard solution described in Example 2 above, and 20 ul of the latex-gel-$P_3G$ dispersion was thereafter added to each pre-mixed phase. The reaction mixture was then poured through a filter made of regenerated cellulose (1 micron) to capture and collect the latex particles. Gold sol particle labelled anti-$P_3G$ antibody was prepared as described in Example II(b) of said co-pending application Ser. No. 105,285, and the gold labelled antibody was suspended in a solution containing 40 mM $MgSO_4$, 1% BSA and 0.02% NaAzide. The mixture was poured through the filter where the latex particles were collected and the filter was washed with a wash solution containing 1.234 mM Thimerosal, 3% Igepal CA720 and 1% sodium dodecyl sulphate in PBS (pH 7.2). The visual results were as follows:

| $P_3G$ (ug/ml) | Reading |
|---|---|
| 0.625 | — |
| 1.25 | — |
| 2.5 | — |
| 5.0 | + (pink color) |
| 10.0 | + (pink color) |
| 20.0 | + (pink color) |

Thus, when the $P_3G$ in the sample exceeded 2.5 ug/ml, the blocking antibody was expended and at least a portion of the $P_3G$ coupled with the latex remained unblocked. After the latex beads were collected on the filter, the unblocked $P_3G$-latex on the filter was able to react with the gold sol particle labelled anti-$P_3G$ antibody, and a collected latex-$P_3G$-anti-$P_3G$-gold immunocomplex was formed. This collected complex on the filter presented a visually observable pink coloration. On the other hand, when the $P_3G$ in the sample was 2.5 ug/ml or less, the blocking antibody was available to block all the $P_3G$-latex and the gold labelled antibody simply remained uncomplexed and in dispersion and in such form that it readily flowed through the filter.

The foregoing Example 3 was repeated using glass particles for the solid phase instead of latex particles, and essentially identical results were obtained.

EXAMPLE 4

Procedures essentially the same as the procedures of Examples 1 through 3 were conducted for assaying for estrone-3-glucuronide ($E_1 3G$). In such assays Bovine Serum Albumin (fraction 5) was used rather than gelatin to link the hapten to the solid support. The BSA linkage procedure is described by Erlanger et al. (supra). The assay results obtained were essentially identical to the results obtained in Examples 1 to 3.

In a practical environment, the $P_3G$ and $E_1 3G$ assays of the present invention may be used to predict ovulation in advance, verify ovulation, assess luteal function, detect the beginning and end of the fertile period assess follicular phase and diagnose pregnancy. The assays may generally be conducted using first morning urine (FMU).

The $P_3G$ assay may be used to measure the increase in $P_3G$ in FMU during ovulation and during the luteal phase and can be calibrated to provide a positive color indication when $P_3G$ rises above the threshold level of about 4 ug/ml. The color (showing $P_3G$ level above 4 ug/ml) remains throughout the luteal phase to indicate the length and adequacy of the ovulation process.

The $E_1 3G$ assay may be used to detect the increase of the $E_1 3G$ level in FMU 3 to 6 days prior to ovulation. The assay is similar to the $P_3G$ assay and may be used to show E 13G levels greater than 30 to 50 ng/ml as an indication that ovulation is imminent.

I claim:

1. An immunoassay procedure to determine the initial presence of at least a prespecified amount of a first immunoreactive substance in a liquid sample said procedure comprising, the steps of:

establishing an immunochemical reaction phase by admixing a liquid sample containing an initially unknown amount of said first immunoreactive substance with (1) a known amount of a second immunoreactive substance that is specifically immunoreactive with said first substance and (2) a quantity of a third immunoreactive substance that has immunological reaction characteristics which are immunospecifically the same as the immunological reaction characteristics of said first immunoreactive substance, said known amount of said second substance being immunochemically equivalent to the total of said prespecified amount of first substance and said quantity of third immunoreactive substance, whereby, when the amount of said first immunoreactive substance in the liquid sample solution exceeds said prespecified amount, unreacted third substance will be available for further immunospecific reaction in the reaction phase;

contacting the thus established reaction phase with a quantity of a fourth immunoreactive substance that has immunological reaction characteristics which are immunospecifically the same as the immunological reaction characteristics of said second substance, said fourth substance carrying a detectable tag; and determining the initial presence of more than said prespecified amount of first substance in said sample by detecting the existence of a specific immunoreaction product containing said detectable tag.

2. A procedure as set forth in claim 1, wherein said third substance is bound to a solid support.

3. A procedure as set forth in claim 2, wherein said solid support comprises a dispersible, particulate, collectible solid material, and said determining includes the step of collecting the collectible material and detecting the presence of said detectable tag in the collected material.

4. A procedure as set forth in claim 3, wherein said collecting comprises capturing the solid collectible material on a filter element.

5. A procedure as set forth in claim 4, wherein said tag comprises a gold sol particle.

6. A procedure as set forth in claim 2, wherein said solid support comprises a permeable membrane, said step of contacting the established reaction phase includes the step of causing a solution containing the fourth substance to flow through the membrane, and said step of determining comprises detecting the presence of said tag on said membrane.

7. A procedure as set forth in claim 6, wherein said tag comprises a gold sol particle.

8. A procedure as set forth in claim 6, wherein said tag comprises a first enzymatic color forming component, there being a corresponding second enzymatic color forming component bound to said membrane adjacent said third substance, the interaction between said first and second enzymatic components causing production of a detectable color on said membrane whenever any fourth substance becomes immunospecifically bound to third substance on the membrane.

9. An immunoassay procedure as set forth in claim 1, wherein said first immunoreactive substance is a therapeutic drug characterized by a therapeutic window.

10. An immunoassay procedure as set forth in claim 1, wherein said first immunoreactive substance is a substance of abuse.

11. An immunoassay procedure as set forth in claim 1, wherein said first immunoreactive substance is characterized by a threshold level.

12. An immunoassay procedure to determine the initial presence of at least a prespecified amount of a first immunoreactive substance in a liquid sample solution, said procedure comprising the steps of:
   providing a liquid sample containing an initially unknown amount of said first immunoreactive substance;
   adding a known amount of a second immunoreactive substance to said sample to produce a first reaction phase, said second immunoreactive substance being immunospecifically reactive with said first immunoreactive substance,
   contacting the first reaction phase with a quantity of a third immunoreactive substance to produce a second reaction phase, said third immunoreactive substance having immunological reaction characteristics which are immunospecifically the same as the immunological reaction characteristics of said first substance,
   said known amount of said second substance being immunochemically equivalent to the total of said prespecified amount of first substance and said quantity of third substance, whereby, when the amount of first substance in the sample solution is greater than said prespecified amount, unreacted third immunoreactive substance will be available for further immunospecific reaction in the second reaction phase;
   bringing the second reaction phase into contact with an amount of a labelled fourth immunoreactive substance to produce a detection phase, said fourth immunoreactive substance having immunological reaction characteristics which are immunospecifically the same as the immunological reaction characteristics of said second substance, whereby a labelled immunoreaction product is formed in said detection phase by the reaction of third and fourth immunoreactive substances whenever unreacted third immunoreactive substance is available for immunospecific reaction in the second reaction phase; and
   detecting the presence of labelled immunoreaction product in said detection phase as an indication of the initial presence of more than said prespecified amount of first immunoreactive substance in the sample.

13. A procedure as set forth in claim 12, wherein said third substance is bound to a solid support.

14. A procedure as set forth in claim 13, wherein said solid support comprises a dispersible, collectible, particulate carrier material, said fourth substance is labelled with a gold sol particle tag, and said detecting step includes the step of collecting the gold sol tag labelled immunoreaction product on a filter element and observing the resultant coloration of the element caused by collection of gold sol particles thereon.

15. A procedure as set forth in claim 12, wherein said first and third substances are each haptens and said second and fourth substances are each anti-hapten antibodies which are specifically immunoreactive with said haptens.

16. A procedure as set forth in claim 15, wherein each said hapten is pregnanediol-3-glucuronide.

17. A procedure as set forth in claim 15, wherein each said hapten is estrone-3-glucuronide.

18. A procedure as set forth in claim 14, wherein each of said first and third substances is a hapten and each of said second and fourth substances are specific anti-hapten antibodies thereto.

19. A procedure as set forth in claim 18, wherein each said hapten is pregnanediol-3-glucuronide.

20. A procedure as set forth in claim 18, wherein each said hapten is estrone-3-glucuronide.

21. An immunoassay procedure as set forth in claim 12, wherein said first immunoreactive substance is a therapeutic drug characterized by a therapeutic window.

22. An immunoassay procedure as set forth in claim 12, wherein said first immunoreactive substance is a substance of abuse.

23. An immunoassay procedure as set forth in claim 12, wherein said first immunoreactive substance is characterized by a threshold level.

24. An immunoassay procedure as set forth in claim 14, wherein said first immunoreactive substance is a therapeutic drug characterized by a therapeutic window.

25. An immunoassay procedure as set forth in claim 14, wherein said first immunoreactive substance is a substance of abuse.

26. An immunoassay procedure as set forth in claim 14, wherein said first immunoreactive substance is characterized by a threshold level.

27. An immunoassay procedure for determining the amount of a first immunoreactive substance in a liquid sample, said procedure comprising the steps of:
   furnishing a liquid sample containing an initially unknown amount of said first immunoreactive substance;
   dividing said sample into a plurality of aliquot portions;
   introducing respective different amounts of a second immunoreactive substance that is specifically immunoreactive with said first immunoreactive substance into said portions to produce a plurality of first reaction phases, each containing a respective different known amount of said second substance;
   contacting each of said first reaction phases with a quantity of a third immunoreactive substance that has immunological reaction characteristics that are immunospecifically the same as the immunological reaction characteristics of said first immunoreactive substance, to thereby produce a plurality of second reaction phases, each containing the same amount of said third substance and respective different amounts of said second substance,
   the respective known amount of said second substance in each of said second reaction phases being predetermined so as to be immunochemically equivalent to the total of said quantity of third substance plus a corresponding respective preselected amount of first substance, whereby, when the unknown amount of said first substance in said sample is less than or equal to said corresponding respective preselected amount thereof, no unreacted third substance will be available for further immunospecific reaction in the corresponding second reaction phase, and when the unknown amount of said first substance in said sample is greater than said corresponding respective preselected amount thereof, unreacted third substance will be available for further immunospecific reaction in the corresponding second reaction phase;

bringing each of said second reaction phases into contact with a quantity of a labelled fourth immunoreactive substance having immunological reaction characteristics that are immunospecifically the same as the immunological reaction characteristics of said second substance, to thereby produce a plurality of respective detection phases corresponding respectively to said second reaction phases, whereby a labelled immunoreaction product will be formed by specific immunoreaction between unreacted third substance and labelled fourth substance in each reaction phase which corresponds to a second phase wherein the amount of first substance in the sample exceeds the said corresponding respective preselected amount thereof; and detecting the presence or absence of labelled immunoreaction product in each detection phases as an indication of the initial presence of at least the corresponding respective preselected amount of first substance in the sample.

28. An immunoassay procedure as set forth in claim 27, wherein said first immunoreactive substance is a therapeutic drug characterized by a therapeutic window.

29. An immunoassay procedure as set forth in claim 27, wherein said first immunoreactive substance is a substance of abuse.

30. An immunoassay procedure as set forth in claim 27, wherein said first immunoreactive substance is characterized by a threshold level.

31. A kit of materials for conducting an immunoassay procedure to detect the presence of at least a predetermined amount of a first immunoreactive substance in a liquid sample, said kit comprising:

a known amount of second immunoreactive substance that is specifically immunoreactive with said first substance;

a known amount of a third immunoreactive substance that has immunological reaction characteristics which are immunospecifically the same as the immunological reaction characteristics of said first immunoreactive substance;

an amount of a labelled fourth immunoreactive substance, said fourth immunoreactive substance having immunological reaction characteristics which are immunospecifically the same as the immunological reaction characteristics of said second substance.

32. A kit as set fourth in claim 31, wherein said third immunoreactive substance is bound to a solid support.

33. A kit as set forth in claim 32, wherein said solid support comprises a dispersible, particulate, collectible solid material.

34. A kit as set forth in claim 31, wherein said fourth immunoreactive substance is labelled using a gold sol particle tag.

35. A kit as set forth in claim 31, for detecting the presence of a hapten in said sample, wherein said second and fourth immunoreactive substances comprise anti-hapten antibodies and said third immunoreactive substance co1comprises said hapten 36. A kit as set forth in claim 35, for detecting the presence of pregnanediol-3-glucuronide in a liquid sample, wherein said third immunoreactive substance comprises pregnanediol-3-glucuronide, and said second and fourth immunoreactive substances each comprise anti-pregnanediol-3-glucuronide antibodies.

37. A kit as set forth in claim 35, for detecting the presence of estrone-3-glucuronide in a liquid sample, wherein said third immunoreactive substance comprises estrone-3-glucuronide, and said second and fourth immunoreactive substances each comprise anti-estrone-3-glucuronide antibody.

38. A kit as set forth in claim 31, comprising vessel means for containing a known amount of said sample and facilitating immunoreaction between immunoreactive substances present therein.

39. A kit as set forth in claim 38, comprising means for collecting immunoreaction products formed in said vessel means.

40. A kit as set forth in claim 39, wherein said means for collecting comprising a filter element.

41. A kit as set forth in claim 31, for detecting the presence of a therapeutic drug, wherein said second and fourth immunoreactive substances each comprise antibodies to said drug and said third immunoreactive substance comprises said drug.

42. A kit as set forth in claim 31, for detecting the presence of a substance of abuse, wherein said second and fourth immunoreactive substances each comprise antibodies to said substance of abuse and said third immunoreactive substance comprises said substance of abuse.

* * * * *

UNITED STATES PATENT AND TRADEMARK OFFICE
CERTIFICATE OF CORRECTION

PATENT NO. : 4,952,517
DATED : August 28, 1990
INVENTOR(S) : IZAK BAHAR

It is certified that error appears in the above-identified patent and that said Letters Patent is hereby corrected as shown below:

Title Page [56] References Cited - U.S. PATENT DOCUMENTS

Please ADD

| | | | |
|---|---|---|---|
| -- 3646346 | 2/29/72 | Catt | 250/83 |
| 3879262 | 4/22/75 | Schuurs et al. | 195/63 |
| 3981981 | 9/21/76 | Reunanen | 424/1.5 |
| 4016250 | 4/5/77 | Saxena | 424/1 |
| 4066512 | 1/3/78 | Lai et al. | 195/127 |
| 4067959 | 1/10/78 | Bolz | 424/1 |
| 4092408 | 5/30/78 | Litt | 424/1 |
| 4098876 | 7/4/78 | Piasio et al. | 424/1 |
| 4378428 | 3/29/83 | Farina et al. | 435/7 |
| 4442204 | 4/10/84 | Greenquist et al. | 435/7 |
| 4450239 | 5/22/84 | Chatterton | 436/510 |
| 4506009 | 3/19/85 | Lenhoff et al. | 435/7 |
| 4508830 | 4/2/85 | Baker et al. | 436/510--; |

FOREIGN PATENT DOCUMENTS

-- PCT/US85/00870       PCT
     PCT/GB86/00670       PCT
     0086095            8/1983  European Patent Off.--.

Column 1, line 64, after "1987" insert --(now United States Letters Patent No. 4,859,612)--.

Column 3, line 23, "P3G" should be --$P_3G$--;
           line 52, "articular" should be --particular--.

Column 7, line 46, "o" should be --or--.

UNITED STATES PATENT AND TRADEMARK OFFICE
CERTIFICATE OF CORRECTION

PATENT NO. : 4,952,517

DATED : August 28, 1990

INVENTOR(S) : IZAK BAHAR

It is certified that error appears in the above-identified patent and that said Letters Patent is hereby corrected as shown below:

Column 14, line 11, after "substance," insert --the third substance being capable of forming an immunocomposite that is separable from the reaction mixture,--.

Column 15, line 22, after "substance," insert --the third substance being capable of forming an immunocomposite that is separable from the reaction mixture,--.

Column 16, line 48, after "substance," insert --the third substance being capable of forming an immunocomposite that is separable from the reaction mixture,--.

Signed and Sealed this

Third Day of November, 1992

Attest:

DOUGLAS B. COMER

*Attesting Officer*     Acting Commissioner of Patents and Trademarks